US007634997B2

(12) United States Patent
Shiue

(10) Patent No.: US 7,634,997 B2
(45) Date of Patent: Dec. 22, 2009

(54) SNORKEL WITH MASK STRAP RETAINING DEVICE

(75) Inventor: Chih-Cheng Shiue, Escondido, CA (US)

(73) Assignee: QDS Injection Molding LLC, San Diego, CA (US)

(*) Notice: Subject to any disclaimer, the term of this patent is extended or adjusted under 35 U.S.C. 154(b) by 709 days.

(21) Appl. No.: 11/492,786

(22) Filed: Jul. 26, 2006

(65) Prior Publication Data

US 2007/0295330 A1 Dec. 27, 2007

(51) Int. Cl.
*A61M 11/00* (2006.01)

(52) U.S. Cl. ............................ 128/201.11; 128/201.27

(58) Field of Classification Search ............ 128/200.24, 128/201.11, 201.27, 201.22; 24/114.5, 3.1, 24/3.13
See application file for complete search history.

(56) References Cited

U.S. PATENT DOCUMENTS

| | | | | | |
|---|---|---|---|---|---|
| 1,309,150 | A | * | 7/1919 | Monfort | 24/3.1 |
| 1,363,709 | A | * | 12/1920 | Bernier | 24/3.1 |
| 3,051,170 | A | * | 8/1962 | Benzel | 128/201.11 |
| 3,233,801 | A | * | 2/1966 | Schulenberg | 224/176 |
| 4,907,582 | A | * | 3/1990 | Meyerrose | 128/201.11 |
| 5,020,191 | A | * | 6/1991 | Uke | 24/3.1 |
| 6,363,929 | B1 | * | 4/2002 | Winefordner et al. | 128/201.11 |
| 2006/0272635 | A1 | * | 12/2006 | Shiue | 128/201.11 |

* cited by examiner

*Primary Examiner*—Steven O Douglas

(57) ABSTRACT

A snorkel comprising a breathing tube and a retaining device formed on the breathing tube. The retaining device includes an elongated fastening strap having a bottom end formed integrally with the breathing tube, and a top end formed with a large first hole and a small second hole being in communication with the first hole; and a button formed integrally with the breathing tube and disposed in a position about flush with the top end of the fastening strap. The button is adapted to secure to the fastening strap by passing through the first hole and locking in the second hole in response to passing a mask strap through a gap between the fastening strap and the breathing tube.

3 Claims, 2 Drawing Sheets

SNORKEL WITH MASK STRAP RETAINING DEVICE

BACKGROUND OF THE INVENTION

1. Field of Invention

The present invention relates to a device for retaining the strap of a face mask including an eye covering (called mask hereinbelow) to a breathing tube of snorkel used for swimming, surface diving, scuba diving or other water activities, and more particularly to a retaining device formed integrally with a breathing tube of snorkel for quickly retaining a mask strap or disengaging therewith.

2. Related Art

Conventionally, a diver may wear a mask and a snorkel when engaging in swimming, surface diving, scuba diving or other water activities. Also, a retaining device is formed or mounted on a predetermined position of a breathing tube. The retaining device is adapted to retain a mask strap and thus allows a diver to easily fit a mouthpiece of the breathing tube in the mouth of the diver. A top open end of the breathing tube is formed as an opening as the mouth of an air passage while a diver wears a snorkel in diving. The snorkel is still attached to the mask strap in an unused state such that they are ready to be worn by a diver. Alternatively, a diver may detach the mask strap from the retaining device in a storage state.

A snorkel having a conventional retaining device A is shown in FIG. 1. The retaining device A is mounted on a breathing tube. The retaining device A is adapted to retain a mask strap B or detach therefrom.

Another prior art retaining device is formed as two separate members in which one member is mounted on a breathing tube and the other member is formed with a mask strap. One member can retain the other member for assembling the snorkel and the mask strap together or detach therefrom for disengagement.

However, the prior art mask strap retaining device suffered from a couple of disadvantages. For example, its assembling or disassembling operation is relatively difficult. Further, its construction is relatively complicated. Thus, the need for improvement still exists.

SUMMARY OF THE INVENTION

It is therefore an object of the present invention to provide a retaining device capable of quickly securely retaining a mask strap to a breathing tube of a snorkel or disengaging therewith.

In one aspect of the present invention the retaining device comprises a fastening strap and a button adapted to easily secure thereto or detach therefrom.

In another aspect of the present invention the fastening strap is resilient such that it is possible of lengthening the fastening strap by pulling in order to secure to the button or detaching therefrom by a reverse operation.

The above and other objects, features and advantages of the present invention will become apparent from the following detailed description taken with the accompanying drawings.

DETAILED DESCRIPTION OF THE INVENTION

Figure 1:
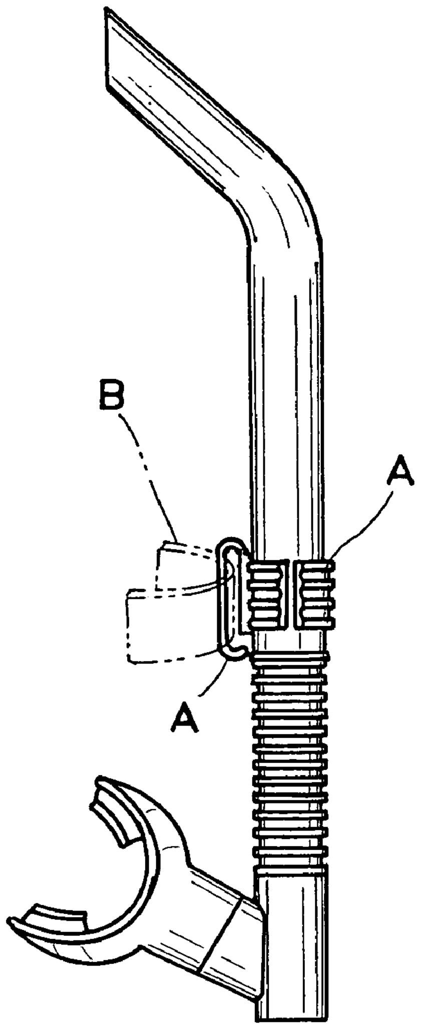
FIG. 1 (PRIOR ART)
FIG. 1 is a side elevation of a conventional snorkel equipped with a mask strap retaining device.
Figure 2:
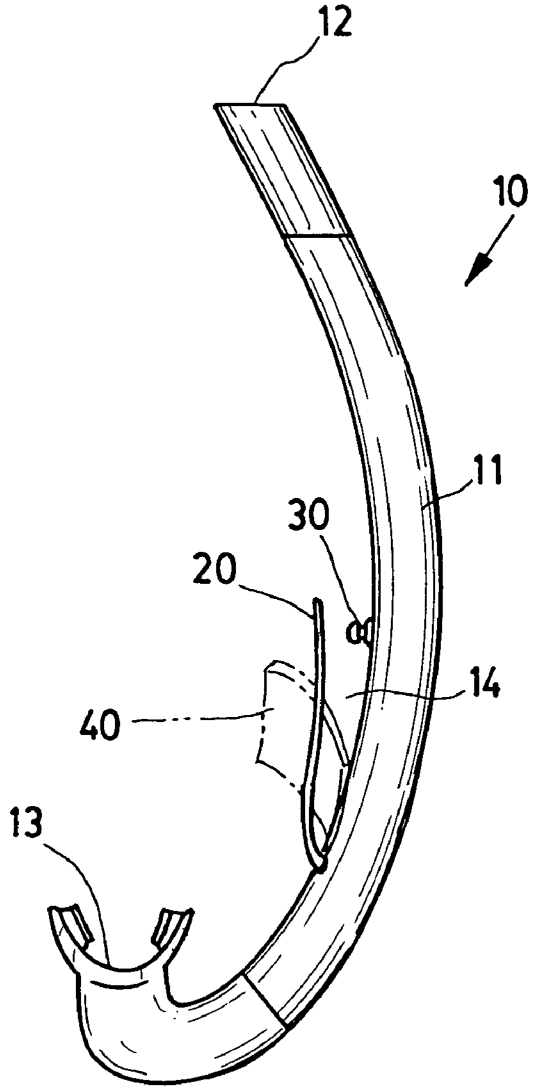
FIG. 2 is a side elevation of a preferred embodiment of snorkel equipped with a mask strap retaining device according to the invention, where a mask strap is engaged with the retaining device but not secured.

Referring to FIG. 2, a snorkel 10 having a mask strap retaining device in accordance with a preferred embodiment of the invention is shown. The retaining device is integrally formed with a breathing tube 11 of the snorkel 10 and comprises a fastening strap 20 and a button 30.

The breathing tube 11 of the snorkel 10, the fastening strap 20, and the button 30 are formed of a flexible plastic material. Further, the fastening strap 20 is slightly resilient in nature.

The snorkel 10 is a tubular member and is well known in the art. In addition to the breathing tube 11, the snorkel 10 further comprises a top opening 12 as the mouth of an air passage, and a bottom mouthpiece 13 for fitting in the mouth such that a diver may use the mouthpiece 13 to inhale and exhale while diving. An open space 14 is defined by the fastening strap 20 joined the breathing tube 11 and the button 30. A mask strap 40 is adapted to pass through the space 14 for mounting. The retaining device is formed on a predetermined position of the breathing tube 11. The retaining device is adapted to retain the mask strap 40 or detach therefrom. As stated above, the retaining device comprises the fastening strap 20 and the button 30. It is noted that the button 30 of the retaining device may has a configuration other than that shown in FIGS. 2 and 3 in other embodiments as long as the button 30 is mounted on or formed with the breathing tube 11 of the snorkel 10 and the button 30 is adapted to secure to an open end 22 of the fastening strap 20 or detach therefrom.

Figure 3:
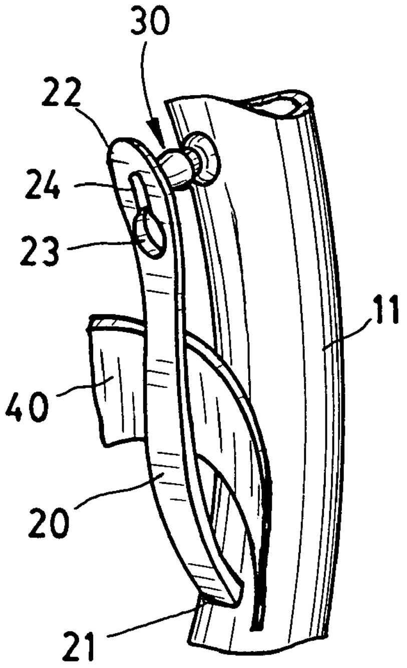
FIG. 3 is a perspective view of an enlarged portion of the snorkel of FIG. 2 for showing the retaining device and the mask strap being in an engaged but not secured state.
Figure 4:
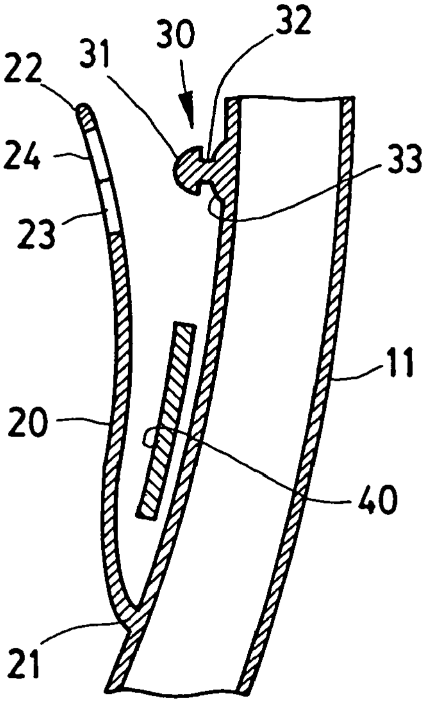
FIG. 4 is a longitudinal sectional view of FIG. 3.

Referring to FIGS. 3 and 4 in conjunction with FIG. 2, the fastening strap 20 is an elongated strap and is slightly resilient in nature. A bottom end 21 of the fastening strap 20 is formed with the breathing tube 11. The top end 22 of the fastening strap 20 is open with a second hole 24 and a first hole 23 larger than the second hole 24 formed thereat. Further, the holes 23 and 24 are in communication each other. The provision of the holes 23 and 24 aims at cooperating with the button 30 to secure the top end 22 of the fastening strap 20 to the button 30 with the mask strap 40 passing through the space 14 defined between the fastening strap 20 and the breathing tube 11.

The button 30 is integrally formed with the breathing tube 11 and is disposed in a position slightly higher than the first hole 23 at the top end 22 of the fastening strap 20. Thus, the button 30 can insert into the first hole 23 after slightly lengthening the fastening strap 20 by pulling. The button 30 comprises an enlarged, round head 31, a narrow neck 32, and a protruding base 33. The head 31 has a diameter slightly smaller than that of the circular first hole 23. The neck 32 has a width slightly smaller than that of the slit-like second hole 24. The base 33 is integrally formed with the breathing tube 11. The base 33 has a width slightly larger than that of the slit-like second hole 24. The fastening strap 20 and the button 30 are not secured together as shown in FIGS. 3 and 4.

Alternatively, both the fastening strap 20 and the button 30 can be formed integrally with the breathing tube 11 of the snorkel 10 in another embodiment.

Figure 5:
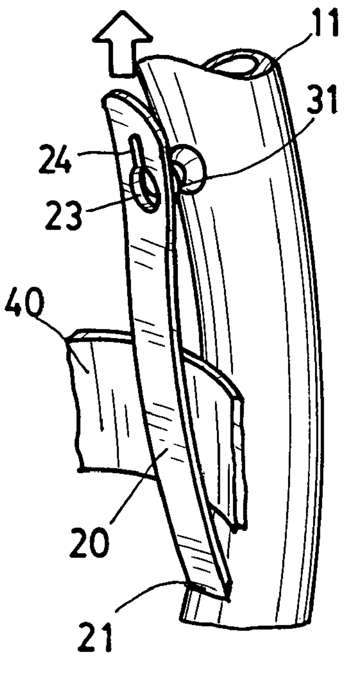
FIGS. 5, 6, and 7 are views similar to FIG. 3 for illustrating three steps of assembling the mask strap and the snorkel together by securing the retaining device to the mask strap.
Figure 6:
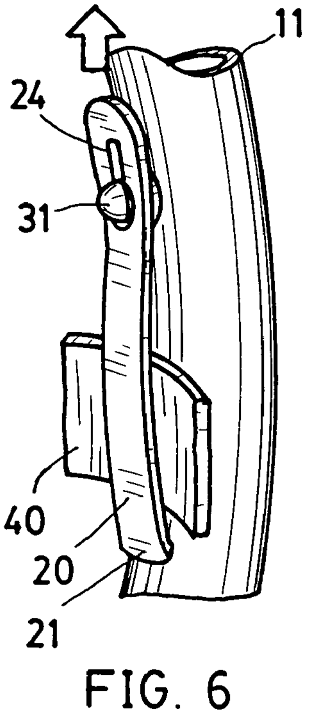
Figure 7:
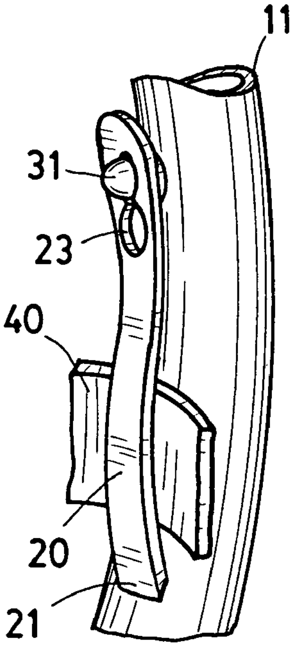

Referring to FIGS. 5, 6, and 7 in conjunction with FIGS. 2 to 4, three steps of assembling the mask strap 40 and the snorkel 10 together by securing the fastening strap 20 to the button 30 are described below.

Referring to FIG. 5, first pass the mask strap 40 through a gap between the fastening strap 20 and the button 30. Next, pull the fastening strap 20 upward to align the head 31 with the first hole 23. Next, press the fastening strap 20 onto the button 30 until the head 31 passes the first hole 23 with the neck 32 engaged with a joining point of a bottom of the second hole 24 and the first hole 23 (see FIG. 6). Next, stop pulling the fastening strap 20 to automatically shorten the fastening strap 20. As a result, the neck 32 moves upward along the second hole 24 until being stopped by a closed top end of the second hole 24 (see FIG. 7). At the position shown in FIG. 7, the fastening strap 20 and the button 30 are secured together because the top end 22 of the fastening strap 20 is fastened by the neck 32 expanding the slit-like second hole 24 and is sandwiched by the front enlarged head 31 and the rear projecting base 33. Also, the mask strap 40 is retained between the fastening strap 20 and the breathing tube 11. Thus, in use a diver may wear the snorkel 10 and a mask (not shown). Next, secure the mask strap 40 to the retaining device on the breathing tube 11 by fastening the fastening strap 20 at the button 30. Finally, attach the mouthpiece 13 to the mouth prior to diving.

To the contrary, for detaching the mask strap 40 from the snorkel 10 a diver may pull the top end 22 of the fastening strap 20 upward to cause the head 31 to move from the second hole 24 to the first hole 23 (i.e., from the position of FIG. 7 to that of FIG. 6). Next, pull the fastening strap 20 outward to cause the head 31 to clear the first hole 23 (see FIG. 2, 3, 4, or 5). As an end, the snorkel 10 and the mask strap 40 are adapted to separate.

In view of above, it is envisaged by the invention that a retaining device for easily and securely attaching a mask strap 40 to a snorkel 10 or detaching them apart is provided.

Note that the fastening strap 20 and the button 30 of the retaining device on the snorkel 10 described above is only a preferred embodiment. Other embodiments different from that shown above are also contemplated by the invention.

While the invention herein disclosed has been described by means of specific embodiments, numerous modifications and variations could be made thereto by those skilled in the art without departing from the scope and spirit of the invention set forth in the claims.

What is claimed is:

1. A snorkel comprising a breathing tube and a retaining device formed on the breathing tube, the retaining device comprising:

an elongated fastening strap having a bottom end formed integrally with the breathing tube, and a top end having a hole fastening member; and a button formed integrally with the breathing tube and disposed in a position about flush with the top end of the fastening strap;

wherein the fastening member is adapted to secure to the button in response to passing a mask strap through a gap between the fastening strap and the breathing tube.

2. The snorkel of claim 1, wherein the fastening member comprises a first hole and a second hole smaller than the first hole and being in communication with the first hole; and the button comprises an enlarged head, a neck, and a base such that (i) pulling the fastening strap to align the head with the first hole, pressing the fastening member onto the button until the head passes the first hole with the neck engaged with a joining point of the second hole and the first hole, and stopping the pulling will automatically shorten the fastening strap to move the neck along the second hole until being stopped will secure the fastening member to the button; or (ii) pulling the fastening strap to cause the head to move from the second hole to the first hole, and pulling the fastening member outward to disengage the first hole with the head will allow the mask strap to detach from the snorkel.

3. The snorkel of claim 1, wherein the fastening strap is formed of a resilient material.

* * * * *